US009504652B2

(12) United States Patent
Filipcsei et al.

(10) Patent No.: US 9,504,652 B2
(45) Date of Patent: Nov. 29, 2016

(54) NANOSTRUCTURED APREPITANT COMPOSITIONS, PROCESS FOR THE PREPARATION THEREOF AND PHARMACEUTICAL COMPOSITIONS CONTAINING THEM

(75) Inventors: Genovéva Filipcsei, Budapest (HU); Zsolt Ötvös, Csongrád (HU); Gábor Heltovics, Budapest (HU); Ferenc Darvas, Budapest (HU)

(73) Assignee: Druggability Technologies IP Holdco (Jersey) Ltd., St. Helier (GB)

( * ) Notice: Subject to any disclaimer, the term of this patent is extended or adjusted under 35 U.S.C. 154(b) by 32 days.

(21) Appl. No.: 13/703,804

(22) PCT Filed: Jun. 17, 2011

(86) PCT No.: PCT/HU2011/000057
§ 371 (c)(1),
(2), (4) Date: Jan. 23, 2013

(87) PCT Pub. No.: WO2011/158053
PCT Pub. Date: Dec. 22, 2011

(65) Prior Publication Data
US 2013/0209521 A1 Aug. 15, 2013

(30) Foreign Application Priority Data
Jun. 18, 2010 (HU) .................................... 1000325

(51) Int. Cl.
*A61K 9/14* (2006.01)
*A61K 31/5377* (2006.01)
*C07D 413/06* (2006.01)

(52) U.S. Cl.
CPC ............. *A61K 9/14* (2013.01); *A61K 31/5377* (2013.01); *C07D 413/06* (2013.01); *Y10T 428/2982* (2015.01)

(58) Field of Classification Search
CPC ... A61K 9/14; A61K 31/5377; C07D 413/06
See application file for complete search history.

(56) References Cited

U.S. PATENT DOCUMENTS

2009/0192161 A1 7/2009 Sawant et al.
2012/0128740 A1 5/2012 Filipcsei et al.
(Continued)

FOREIGN PATENT DOCUMENTS

WO 03/049718 A1 6/2003
WO 2008/104512 A2 9/2008
(Continued)

OTHER PUBLICATIONS

Niesz et al. (Microfluid Nanofluid 2008;5:411-416.*
Ali et al. BASF technical [online] Mar. 3, 2006, 4 pages.*
Ghebremeskel et al. (International Journal of Pharmaceutics 2007;328:119-129).*
(Continued)

*Primary Examiner* — Ernst V Arnold
(74) *Attorney, Agent, or Firm* — Jason D. Voight

(57) ABSTRACT

The present invention is directed to nanostructured Aprepitant compositions, process for the preparation thereof and pharmaceutical compositions containing them. The nanoparticles of Aprepitant according to the invention have an average particle size of less than about 200 nm. The stable nanostructured particles of the invention are presented by increased solubility, dissolution rate, permeability and bioequivalent or enhanced biological performance characterized by significantly decreased fed/fasted effect compared to the reference and marketed drug. Aprepitant is a chemical compound that belongs to a class of drugs called substance P antagonists (SPA). It mediates its effect by acting on neurokinin 1 receptor. Aprepitant is manufactured by Merck & Co. under the brand name Emend for prevention of acute and delayed chemotherapy-induced nausea and vomiting (CINV) and for prevention of postoperative nausea and vomiting.

9 Claims, 5 Drawing Sheets

(56) References Cited

U.S. PATENT DOCUMENTS

| | | |
|---|---|---|
| 2012/0135053 A1 | 5/2012 | Filipcsei et al. |
| 2012/0141561 A1 | 6/2012 | Filipcsei et al. |
| 2012/0148637 A1 | 6/2012 | Filipcsei et al. |
| 2013/0202706 A1 | 8/2013 | Filipcsei et al. |
| 2013/0210794 A1 | 8/2013 | Filipcsei et al. |

FOREIGN PATENT DOCUMENTS

| | | | |
|---|---|---|---|
| WO | 2009/131930 A1 | 10/2009 | |
| WO | WO2009133418 | * 11/2009 | .............. B01J 13/00 |
| WO | 2010/092591 A2 | 8/2010 | |
| WO | 2010/140132 A1 | 12/2010 | |

OTHER PUBLICATIONS

Olver et al.: "Nanomedicines in the treatment of emesis during chemotherapy: focus on aprepitant", International Journal of Nanomedicine, 2007, vol. 2, No. 1, pp. 13-18.

Wu et al.: "The role of biopharmaceutics in the development of a clinical nanoparticle formulation of MK-0869: a Beagle dog model predicts improved bioavailability and diminished food effect on absorption in human", International Journal of Pharmaceutics, 2004, vol. 285, pp. 135-146.

Shono et al.: "Forecasting in vivo oral absorption and food effect of micronized and nanosized aprepitant formulations in humans", European Journal of Pharmaceutics and Biopharmaceutics, 2010, vol. 76, pp. 95-104.

* cited by examiner

NANOSTRUCTURED APREPITANT COMPOSITIONS, PROCESS FOR THE PREPARATION THEREOF AND PHARMACEUTICAL COMPOSITIONS CONTAINING THEM

This is the national stage of International Application PCT/HU2011/000057, filed Jun. 17, 2011.

FIELD OF THE INVENTION

The present invention is directed to nanostructured Aprepitant compositions, process for the preparation thereof and pharmaceutical compositions containing them.

The nanoparticles of Aprepitant according to the invention have an average particle size of less than about 200 nm. The stable nanostructured particles of the invention are presented by increased solubility, dissolution rate, permeability and bioequivalent or enhanced biological performance characterized by significantly decreased fed/fasted effect compared to the reference and marketed drug.

Aprepitant is a chemical compound that belongs to a class of drugs called substance P antagonists (SPA). It mediates its effect by acting on neurokinin 1 receptor. Aprepitant is manufactured by Merck & Co. under the brand name Emend for prevention of acute and delayed chemotherapy-induced nausea and vomiting (CINV) and for prevention of postoperative nausea and vomiting.

BACKGROUND OF THE INVENTION

A. Background Regarding to Nanoparticle Formation/Production

Nowadays, the active ingredient developers run out of new chemical entities with high solubility; most compounds that are approved or enter development processes are poorly soluble and/or have low permeability. The traditional approaches to increase the solubility and dissolution rate of these compounds are very limited. Chemical modification, like salt- or prodrug formation and inclusion of ionizable groups could result in higher performance of the active compounds. However, these structural modifications can lead to inactivity or instability of the active compounds in many cases. Conventional solid or liquid formulations (e.g.; micronization, milling, solid dispersion, liposomes) could also be useful tools for the researchers to increase the solubility of the compounds, but the efficiency of the formulation is far behind the chemical modification. Nevertheless, these conservative approaches are very time- and cost-consuming procedures with high failure rates.

Nanoformulation is currently one of the most progressive fields of the pharmaceutical industry to increase solubility, bioavailability as well as reduce food and side effects of such active ingredients.

Nanoformulation is the reduction of particles size down to below 200 nm. The reduction of particle size leads to significantly increased dissolution rate of the active ingredients, which in turn can lead to increases in bioavailability.

There are two main approaches to making nanoparticles: "top-down" and "bottom-up" technologies. The conventional top-down approach basically relies on mechanical attrition to render large crystalline particles into nanoparticles. The bottom-up approach relies on controlled precipitation. The process involves dissolving the drugs in a solvent and precipitation in a controlled manner to nanoparticles through addition of an antisolvent.

Technologies relying on milling (top-down) or high-pressure homogenization (mixture of uncontrolled-bottom-up and top-down) are cost and time consuming methods. Both processes require high energy. This means that a large number of active compounds cannot be nanoformulated with these approaches due to heat induced active form conversion. For example, salt or active compounds with low melting point cannot be milled or high-pressure homogenized. The scale-up (industrial applicability) of the high energy processes are difficult and limited in many cases. These technologies target only late stage formulation or reformulation of poorly soluble active compounds to improve their efficiency.

Nanoparticle compositions are described, for example, in US 20080214535, WO 2007147160, WO 2008044102, U.S. Pat. Nos. 5,145,684; 5,719,147; 6,048,859; 6,096,742 and 6,235,735 patents.

Process for the preparation of Aprepitant is described, for example, in WO/2008/104512, WO/2007/088483, WO/2007/147160, WO/2007/016582, WO/2007/112457, WO/2009/001203 and WO/2009/108828 patents.

The nanoparticles of active pharmaceutical compounds can be made using, for example, milling, homogenization, precipitation techniques, or supercritical fluid techniques, as is known in the art. Methods of making nanoparticulate compositions are also described in U.S. Pat. No. 5,718,388, U.S. Pat. No. 5,862,999, U.S. Pat. No. 5,665,331, U.S. Pat. No. 5,543,133, U.S. Pat. No. 5,534,270.

B. Background Regarding Aprepitant

Aprepitant is a substance P/neurokinin 1 ($NK_1$) receptor antagonist, chemically described as 5-[[(2R,3S)-2-[(1R)-1-[3,5-bis(trifluoromethyl)phenyl]ethoxy]-3-(4-fluorophenyl)-4-morpholinyl]methyl]-1,2-dihydro-3H-1,2,4-triazol-3-one.

Its empirical formula is $C_{23}H_{21}F_7N_4O_3$, and its structural formula is:

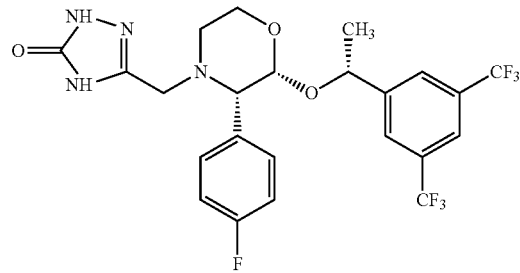 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

Aprepitant is a white to off-white crystalline solid, with a molecular weight of 534.43. It is practically insoluble in water. Aprepitant is sparingly soluble in ethanol and isopropyl acetate and slightly soluble in acetonitrile.

Each capsule of EMEND for oral administration contains either 40 mg, 80 mg, or 125 mg of Aprepitant and the following inactive ingredients: sucrose, microcrystalline cellulose, hydroxypropyl cellulose and sodium lauryl sulfate. The capsule shell excipients are gelatin, titanium dioxide, and may contain sodium lauryl sulfate and silicon dioxide. The 40-mg capsule shell also contains yellow ferric oxide, and the 125-mg capsule also contains red ferric oxide and yellow ferric oxide.

Pharmacokinetics

Absorption

Following oral administration of a single 40 mg dose of EMEND in the fasted state, mean area under the plasma concentration-time curve ($AUC_{0-\infty}$) was 7.8 mcg•hr/mL and mean peak plasma concentration ($C_{max}$) was 0.7 mcg/mL, occurring at approximately 3 hours postdose ($t_{max}$). The absolute bioavailability at the 40-mg dose has not been determined.

Following oral administration of a single 125-mg dose of EMEND on Day 1 and 80 mg once daily on Days 2 and 3, the $AUC_{0-24h}$ was approximately 19.6 mcg•hr/mL and 21.2 mcg•hr/mL on Day 1 and Day 3, respectively. The Cmax of 1.6 mcg/mL and 1.4 mcg/mL were reached in approximately 4 hours ($T_{max}$) on Day 1 and Day 3, respectively. At the dose range of 80-125 mg, the mean absolute oral bioavailability of Aprepitant is approximately 60 to 65%. Oral administration of the capsule with a standard high-fat breakfast had no clinically meaningful effect on the bioavailability of Aprepitant.

Metabolism

Aprepitant undergoes extensive metabolism. In vitro studies using human liver microsomes indicate that Aprepitant is metabolized primarily by CYP3A4 with minor metabolism by CYP1A2 and CYP2C19. Metabolism is largely via oxidation at the morpholine ring and its side chains. No metabolism by CYP2D6, CYP2C9, or CYP2E1 was detected. In healthy young adults, Aprepitant accounts for approximately 24% of the radioactivity in plasma over 72 hours following a single oral 300 mg dose of [$^{14}$C]-Aprepitant, indicating a substantial presence of metabolites in the plasma. Seven metabolites of Aprepitant, which are only weakly active, have been identified in human plasma.

Side Effects

The following side effects have been reported in general use with Aprepitant: allergic reactions, which may be serious, and may include hives, rash and itching and cause difficulty in breathing or swallowing.

Because of the insolubility of Aprepitant in biological relevant media and significant fed/fasted effect, there is a need in the art to enhance bioavailability in the fasted condition/increase the absorption in fasted condition/faster onset of action and reduce the dosage in order to overcome the problems associated with prior conventional Aprepitant formulations. These problems can be solved by novel nanostructured particle formation of Aprepitant characterized by increased solubility/dissolution rate, decreased fed/fasted effect, bioequivalence or higher $C_{max}$ and faster onset of action compared to reference active compound and/or to the marketed drug described in the present invention. The present invention satisfies this need.

DESCRIPTION OF THE INVENTION

Figure 1:
FIG. 1: Comparative dissolution test of reference (unformulated) crystalline Aprepitant and nanostructured Aprepitant.

The present invention describes nanostructured Aprepitant and its pharmaceutical composition with increased solubility/dissolution rate, decreased fed/fasted effect, bioequivalence or higher $C_{max}$ and faster onset of action compared to reference active compound and/or to the marketed drug described in the present invention.

The invention comprises novel nanostructured Aprepitant composition having an average particle size of less than about 200 nm.

The invention comprises a stable nanostructured Aprepitant composition comprising:

(a) nanostructured Aprepitant having an average particle size of less than about 200 nm; and (b) at least one stabilizer and (c) optionally any additional stabilizer for steric and electrostatic stabilization wherein the composition of the invention is prepared preferably in a continuous flow reactor, more preferable in microfluidic based continuous flow reactor.

In the composition of the invention can be used in a phase selected from a crystalline phase, an amorphous phase, a semi-crystalline phase, a semi-amorphous phase, a co-crystal and mixtures thereof.

As exemplified in the examples below, not every combination of stabilizers will result in a stable nanostructured particle formation. It was discovered, that stable nanostructured particles of Aprepitant can be made by continuous flow precipitation method using selected stabilizers.

For the preparation of the composition of the invention stabilizers include nonionic, anionic, cationic, ionic polymers/surfactants and zwitterionic surfactants can be used. Combinations of more than one stabilizer can also be used in the invention. Useful stabilizers which can be employed in the invention include, but are not limited to known organic and inorganic pharmaceutical excipients. Such excipients include various polymers, low molecular weight oligomers, natural products, and surfactants.

Representative examples of stabilizers include hydroxypropyl methylcellulose, hydroxypropylcellulose, polyvinylpyrrolidone, graft copolymer comprised of polyethylene, glycol, polyvinylcaprolactam and polyvinylacetate; sodium lauryl sulfate, gelatin, cetostearyl alcohol, polyethylene glycols, acetic acid, ethenyl ester polymer with 1-ethenyl-2-pyrrolidinone (PVP/VA copolymers), sodium dodecyl benzene sulfonate, tocopheryl polyethylene glycol succinates, urea, citric acid, sodium-acetate, polyethoxylated castor oils and its derivatives, polyoxyethylene stearates, methylcellulose, hydroxyethylcellulose, polyvinyl alcohol (PVA), 4-(1,1,3,3-tetramethylbutyl)-phenol polymer with ethylene oxide and formaldehyde (also known as tyloxapol, superione, and triton), poloxamers (e.g., Pluronics, which are block copolymers of ethylene oxide and propylene oxide); poloxamines (e.g., Tetronic, also known as Poloxamine, which is a tetrafunctional block copolymer derived from sequential addition of propylene oxide and ethylene oxide to ethylenediamine, D-alfa-Tocopherol polyethylene glycol 1000 succinate, poly(2-ethyl-2-oxazoline), poly (methyl vinyl ether), random copolymers of vinyl pyrrolidone and vinyl acetate, such as Plasdone S630 and the like.

Examples of useful ionic stabilizers include, but are not limited to, polymers, biopolymers, polysaccharides, cellulosics, alginates, phospholipids, and nonpolymeric compounds, such as zwitterionic stabilizers, poly-n-methylpyridinium, anthryul pyridinium chloride, cationic phospholipids, chitosan, polylysine, polyvinylimidazole, polybrene, polymethylmethacrylate trimethylammonium-bromide bromide (PMMTMABr), benzalkonium chloride, hexadecyltrimethylammonium bromide, hexyldesyltrimethylammonium bromide (HDMAB), and polyvinylpyrrolidone-2-dimethylaminoethyl methacrylate dimethyl sulfate.

Advantages of the composition of the invention include, but are not limited to: (1) it has bioequivalent pharmacokinetic profile or higher $C_{max}$, AUC (bioavailability) and lower $t_{max}$ compared to the reference and/or marketed drugs; (2) it has increased solubility of Aprepitant in FassiF and FessiF media and (3) increased rate of dissolution for Aprepitant nanostructured particles as compared to conventional forms of the same active compound; (4) it has significantly increased in vitro permeability and decreased fed/fasted effect.

Another aspect of the invention is a process for the preparation of nanostructured Aprepitant comprising mixing an appropriate solvent of Aprepitant with a solution of one or more stabilizers in a continuous flow reactor, preferable in a microfluidic continuous flow reactor.

Preferably the process for the preparation of the composition of the invention is carried out by (1) dissolving Aprepitant and optionally one or more stabilizer in a suitable solvent; (2) adding the formulation from step (1) to a solution comprising at least one stabilizer; and (3) precipitating the formulation from step (2).

Preferably the process for the preparation of the composition of the invention is carried out by (1) dissolving Aprepitant and one or more stabilizer(s) in a suitable solvent; (2) adding the formulation from step (1) to a solution from step (1) to a solvent comprising optionally one or more stabilizer(s); and (3) precipitating the formulation from step (2).

The process is carried out by (a) using two different solvents miscible with each other, where Aprepitant is soluble only in one of them with the restriction that the applied stabilizer(s) is soluble in the solvents used. Such solvents may be dimethyl-sulfoxyde, methanol, ethanol, isopropanol, acetonitrile, tetrahydro-furane, acetone and pyridine preferably.

As a continuous flow reactor preferable a microfluidics based continuous flow reactor, described in the publication Microfluid Nanofluid DOI 10.1007/s 10404-008-0257-9 by I. Hornyak, B. Borcsek and F. Darvas, is used.

The particle size of the nanostructured Aprepitant may be influenced by the solvents used, the flow rate and the Aprepitant—stabilizer ratio.

Another aspect of the invention is directed to the good/instantaneous redispersibility of solid nanostructured form of Aprepitant in biologically relevant mediums, e.g.; physiological saline solution, pH=2.5 HCl solution, FessiF and FassiF media.

Another aspect of the invention is a pharmaceutical composition comprising a stable nanostructured Aprepitant or composition of them according to the invention and optionally pharmaceutically acceptable auxiliary materials.

The pharmaceutical composition of the invention can be formulated: (a) for administration selected from the group consisting of oral, pulmonary, rectal, colonic, parenteral, intracisternal, intravaginal, intraperitoneal, ocular, otic, local, buccal, nasal, and topical administration; (b) into a dosage form selected from the group consisting of liquid dispersions, gels, aerosols, ointments, creams, lyophilized formulations, tablets, capsules; (c) into a dosage form selected from the group consisting of controlled release formulations, fast melt formulations, delayed release formulations, extended release formulations, pulsatile release formulations, and mixed immediate release and controlled release formulations; or (d) any combination of (a), (b), and (c).

The compositions can be formulated by adding different types of excipients for oral administration in solid, liquid, local (powders, ointments or drops), or topical administration, and the like.

A preferred dosage form of the invention is a solid dosage form, although any pharmaceutically acceptable dosage form can be utilized.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents, or vehicles including water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

Solid dosage forms for oral administration include, but are not limited to, capsules, tablets, pills, powders, and granules. In such solid dosage forms, the active agent is admixed with at least one of the following: (a) one or more inert excipients (or carriers), such as sodium citrate or dicalcium phosphate; (b) fillers or extenders, such as starches, lactose, sucrose, glucose, mannitol, and silicic acid; (c) binders, such as carboxymethylcellulose, alginates, gelatin, 35 polyvinylpyrrolidone, sucrose, and acacia; (d) humectants, such as glycerol; (e) disintegrating agents, such as agar-agar, calcium carbonate, potato or tapioca starch, alginic acid, certain complex silicates, and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and j) lubricants, such as talc, calcium stearate, magnesium stearate, solid polyethylene glycols, sodium lauryl sulfate, or mixtures thereof. For capsules, tablets, and pills, the dosage forms may also comprise buffering agents.

Besides such inert diluents, the composition can also include adjuvants, such as wetting agents, emulsifying and suspending agents, sweetening, flavoring, and perfuming agents.

The pharmaceutical compositions of the invention disclosed herein show enhanced lipophilicity/bioavailability/bioequivalent or increased absorption and increased solubility/dissolution rate/reduced side effect/faster onset of action/decreased fed/fasted effect. The compositions of the invention can be used in a decreased dose for the prevention of acute and delayed chemotherapy-induced nausea and vomiting (CINV) and for the prevention of postoperative nausea and vomiting.

A. Preferred Characteristics of the Aprepitant Nanoparticles of the Invention

Increased Solubility and Dissolution Rate of Nanostructured Aprepitant

Nanostructured Aprepitant compositions of the invention have increased solubility and dissolution profile along with increased in vitro PAMPA permeability and reduced ratio of PAMPA permeability when the nanoformulation is redispersed in FeSSIF and FaSSIF biorelevant media due to the decreased particles size and nanostructured particle formation.

Example 1

Instantaneous Wettability and Redispersibility of Nanostructured Aprepitant

Dissolution tests were performed by redispersing 4.0 mg reference Aprepitant, 24.0 mg nanostructured Aprepitant powder containing 4.0 mg Aprepitant in 8.0 mL distillate water. The suspension was stirred for 10 minutes.

Due to the instantaneous wettability and redispersibility of the nanostructured Aprepitant solid powder it formed a colloid solution, while crystals of reference Aprepitant did not wet and did not dissolve (FIG. 1.).

FIG. 1.: Comparative dissolution test of reference Aprepitant and nanostructured Aprepitant

Example 2

Redispersibility Test of Nanostructured Aprepitant

Redispersibility test was performed by redispersing nanostructured Aprepitant powder in distillate water. 3.0 mg freeze dried nanostructured Aprepitant was redispersed in 1.0 mL distillate water under vigorous stirring. The particles size of the redispersed sample was measured by DLS method (Nanotrac instrument, Mictrotrac Co., USA).

Figure 2:
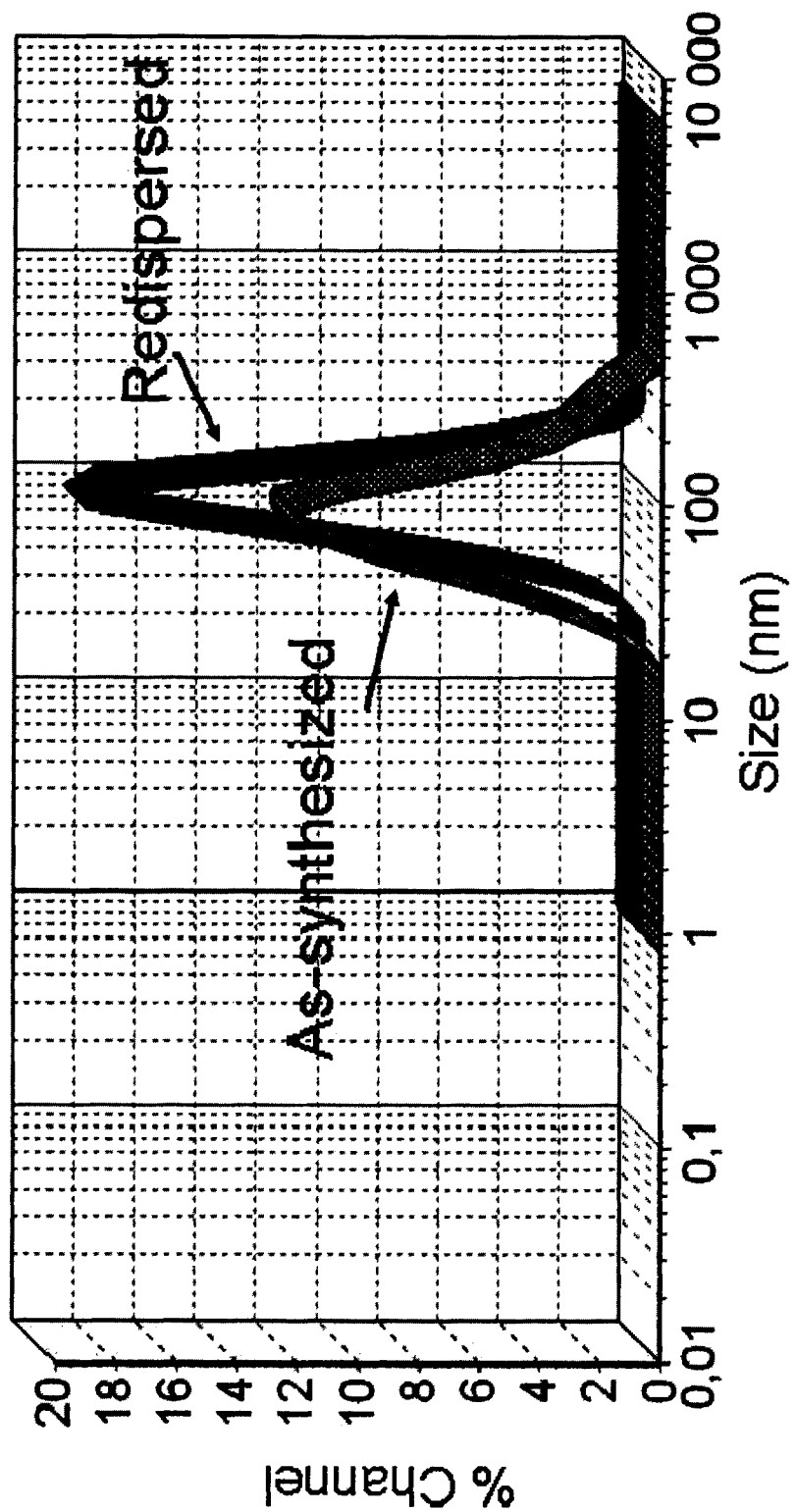
FIG. 2: Size and size distribution of the Aprepitant nanoparticles before (as-synthesized) and after its redispersion.

The mean particle size of redispersed nanostructured Aprepitant (intensity-based average) is d(50)=79 nm, while d(90) value is 198 nm as demonstrated in FIG. 2.

The significant benefit which can be obtained by nanoformulation is that the Aprepitant nanoparticles of the present invention can be redispersed after the drying/solid formulation procedure having similar average particle size. Having the similar average particles size after the redispersion, the dosage form cannot lose the benefits afforded by the nanoparticle formation. A nanosize suitable for the present invention is an average particle size of less than about 200 nm.

FIG. 2: Size and size distribution of the Aprepitant the nanoparticles before (as-synthesized) and after its redispersion.

Example 3

Crystallographic Structure of Nanostructured Aprepitant Composition of the Invention The chemical stability of solid drugs is affected by the crystalline state of the drug. Many drug substances exhibit polymorphism. Each crystalline state has different chemical reactivity. The stability of drugs in their amorphous form is generally lower than that of drugs in their crystalline form, because of the higher free-energy level of the amorphous state. Decreased chemical stability of solid drugs brought about by mechanical stresses such as grinding is to a change in crystalline state. The chemical stability of solid drugs is also affected by the crystalline state of the drug through differences in surface area. For reaction that proceeds on the solid surface of the drug, an increase in the surface area can increase the amount of drug participating in the reaction.

The structure of the Aprepitant nanoparticles was investigated by X-ray diffraction analysis (Philips PW1050/1870 RTG powder-diffractometer). It was surprisingly found that the controlled nano-precipitation of Aprepitant in the presence of the selected stabilizer(s) resulted in stable amorphous nanostructured Aprepitant particle formation which can be characterized by increased solubility and dissolution rate compared to the reference and marketed active compounds. The X-ray diffractograms are demonstrated in FIG. 3.

Figure 3:
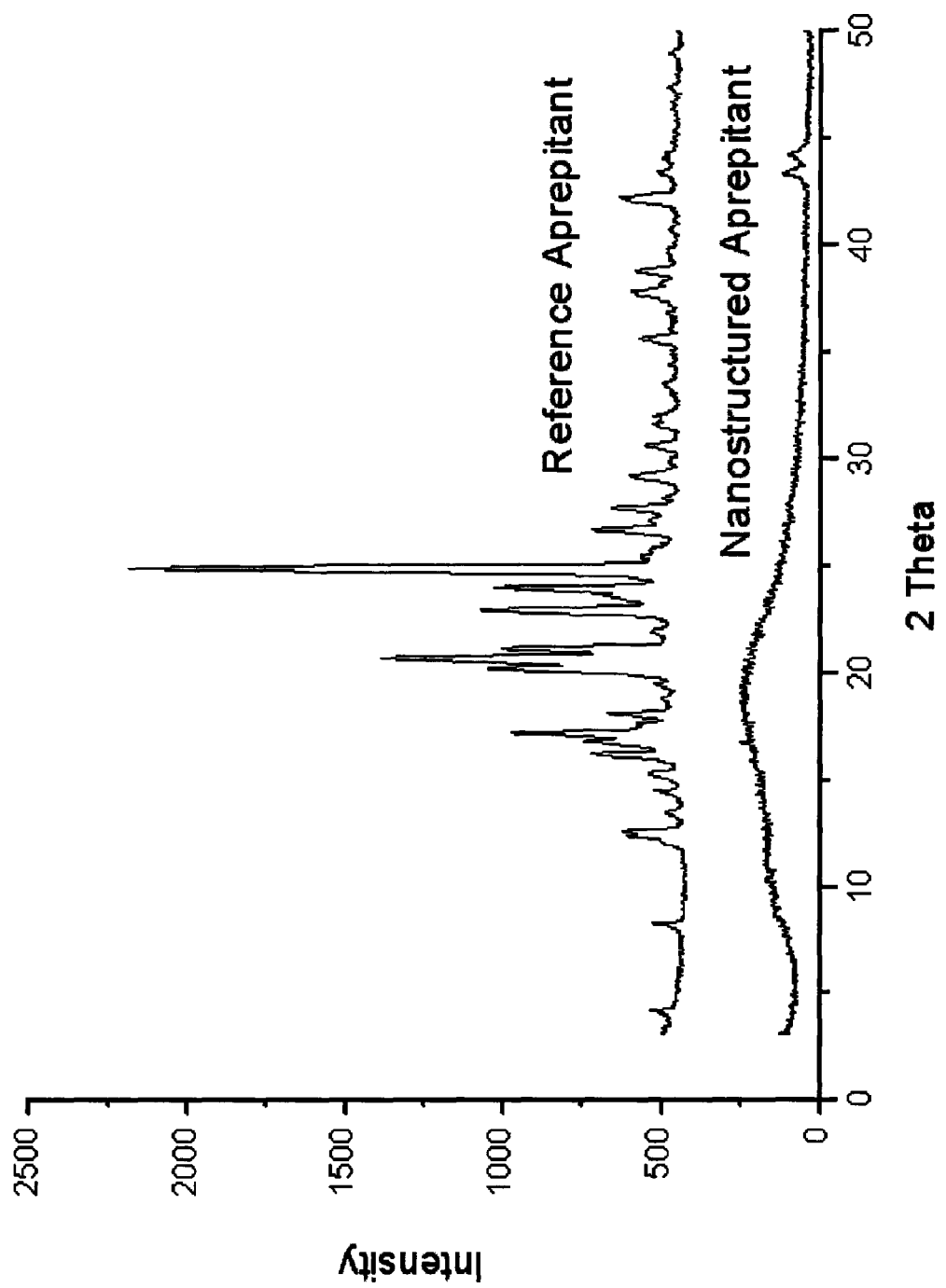
FIG. 3: X-ray diffractograms of reference (unformulated) crystalline Aprepitant and nanostructured Aprepitant of the invention.

FIG. 3: X-ray diffractograms of reference Aprepitant and nanostructured Aprepitant of the invention

Example 4

Determination of $C_{max}$

The solubility of nanostructured Aprepitant compared to the reference and marketed form of the active compound was determined in FassiF and Fessif media by UV-VIS measurements at 271 nm wavelength and room temperature. The redispersed sample was filtered through a 100 nm disposable syringe filter.

Figure 4:
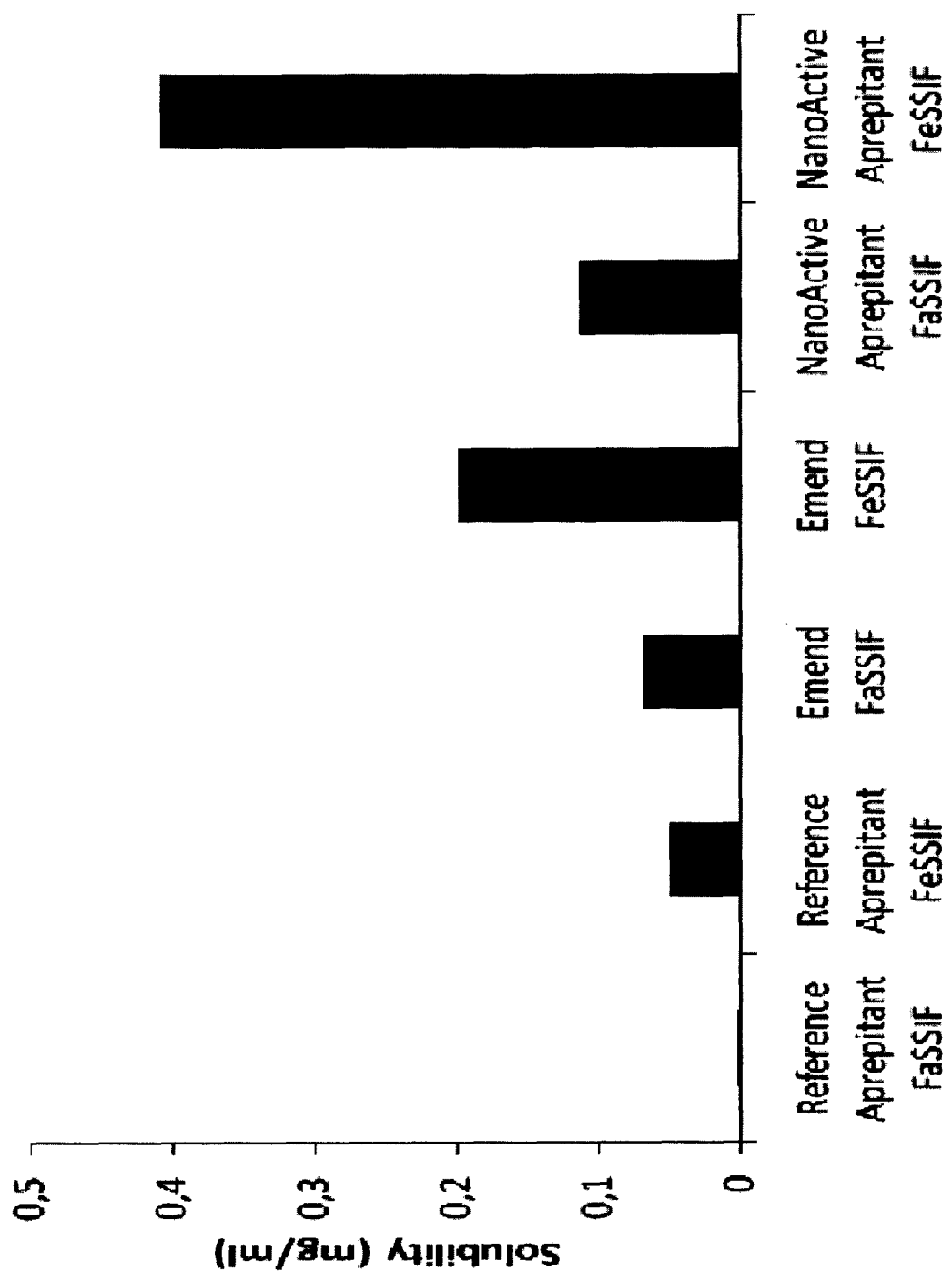
FIG. 4: Solubility enhancement of Aprepitant by nanoformulation.

The solubility of nanostructured Aprepitant was 0.112 mg/mL and 0.409 in FaSSIF and FeSSiF, respectively which is 242 and 8 time higher than the solubility of the reference Aprepitant in FaSSIF and FeSSIF, respectively, and 1.6 and 2.1 times higher than the solubility of the marketed form in FaSSIF and FeSSIF, respectively as shown in FIG. 4.

FIG. 4.: Solubility enhancement of Aprepitant by nanoformulation

Example 5

PAMPA Permeability

In order to demonstrate the improved pharmacokinetic properties of the novel nanostructured Aprepitant PAMPA permeability measurements were performed. Reference Aprepitant, the marketed form and solid nanostructured Aprepitant was redispersed in FaSSIF or in FeSSIF biorelevant media and permeability was measured across and artificial membrane composed of dodecane with 20% soy lecithin. The sample containing the reference compound was a suspension of crystals visible by the naked eye, while the other two samples were opalescent colloid solutions. The receiver compartment was phosphate buffered saline with 1% sodium lauryl sulphate and 5% DMSO.

The PAMPA permeability of the reference compound was $0.044*10^{-6}+/-0.014*10^{-6}$ cm/s and $0.471*10^{-6}+/-0.043*10^{-6}$ cm/s when redispersed in FaSSIF and FeSSIF, respectively. The ratio of PAMPA permeability for FeSSSIF and FaSSIF was 10.7. These in vitro results are in good agreement with low in vivo Aprepitant bioavailability in the fasted state and significantly higher in the fed state ($AUC_{Fed/Fasted}$=5.1) reported earlier by the manufacturer of the marketed formula (www.elandrugtechnologies.com).

For the marked form PAMPA permeability was $0.287*10^{-6}+/-0.033*10^{-6}$ cm/s and $1.614*10^{-6}+/-0.067*10^{-6}$ cm/s when redispersed in FaSSIF and FeSSIF, respectively. The ratio of PAMPA permeability for FeSSSIF and FaSSIF was 5.6. The improved PAMPA between the experiments where permeability in both media and the reduction of the ratio of PAMPA permeability FaSSIF and FeSSIF was used for redispersing media is in good agreement with improved absorption and reduced food effect ($AUC_{Fed/Fasted}$=1.2) reported earlier by the manufacturer of the marketed formula (www.elandrugtechnologies.com).

The PAMPA permeability of the novel nanostructured formula was $1.643*10^{-6}+/-0.115*10^{-6}$ cm/s and $4.645*10^{-6}+/-0.095*10^{-6}$ cm/s when redispersed in FaSSIF and FeSSIF, respectively.

The ratio of PAMPA permeability for FeSSIF and FaSSIF was 2.8. Based on the improved PAMPA permeability of the nanostructured Aprepitant when compared to the marketed form and the good correlation between PAMPA permeability and in vivo data reported earlier we concluded that the nanostructured Aprepitant could have superior pharmacokinetic properties (higher bioavailability, earlier $t_{max}$, higher $c_{max}$, lower fed/fasted ratio) when compared to the marketed form.

Figure 5:
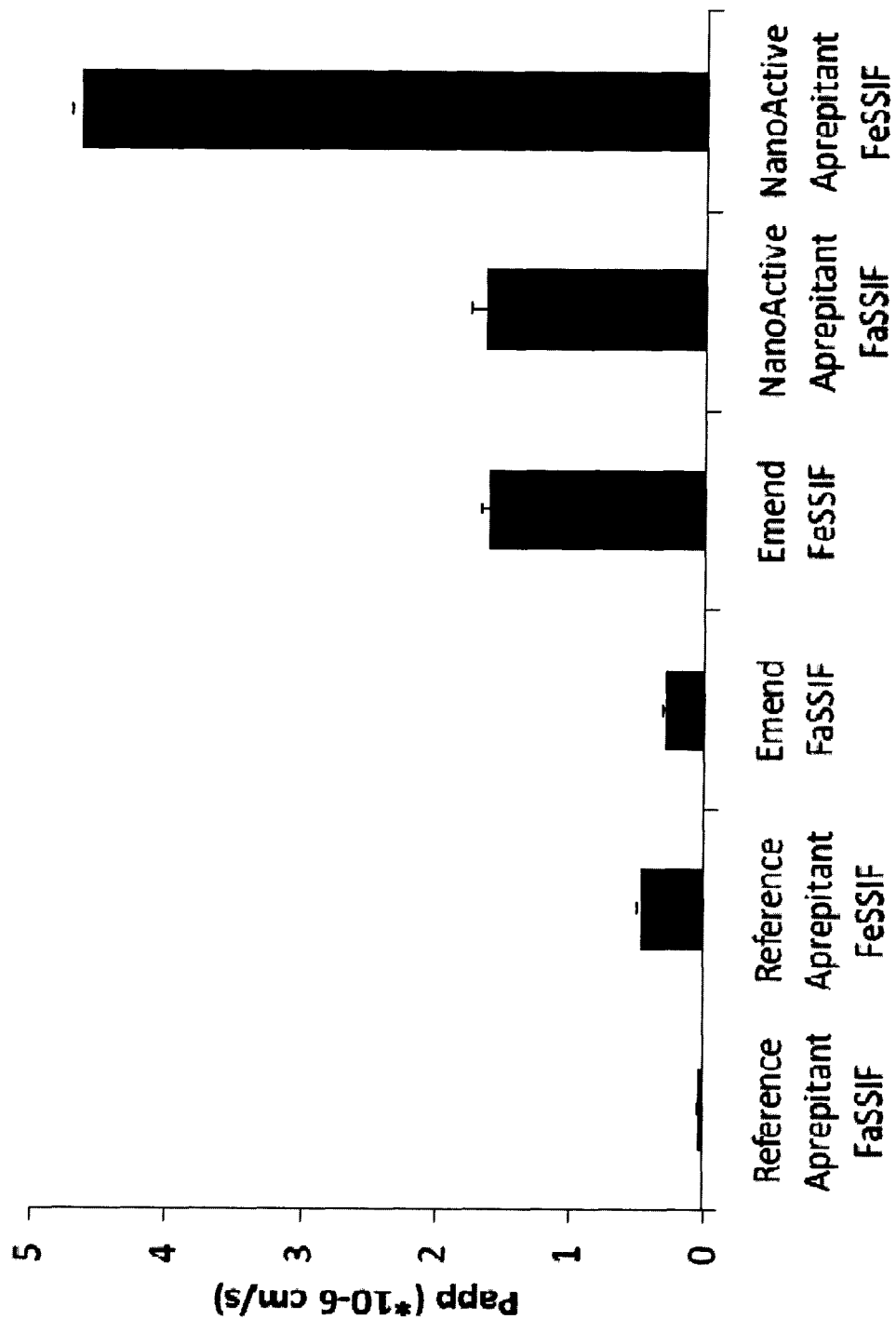
FIG. 5: PAMPA permeability enhancement of Aprepitant by nanoformulation.

FIG. 5.: PAMPA permeability enhancement of Aprepitant by nanoformulation

B. Compositions

The nanoparticles of Aprepitant and its compositions according to the invention have an average particle size of less than about 200 nm. The stable nanostructured particles of the present invention are characterized by increased solubility, dissolution rate and bioequivalent or superior biological performance, reduces fed/fasted effect compared to the reference and marketed forms.

The stabilizers preferably are associated or interacted with the Aprepitant and its pharmaceutically acceptable salts, but do not chemically react with the Aprepitant or themselves.

The nanoparticles of Aprepitant of the invention can be prepared by solvent-antisolvent nano-precipitation methods using stabilizer(s).

Particle Size of the Nanostructured Aprepitant Particles

The invention contains Aprepitant nanoparticles, which have an average particle size of less than about 200 nm as measured by dynamic light scattering method.

By "an average particle size of less than about 200 nm" it is meant that at least 50% of Aprepitant and its pharmaceutically acceptable salts have a particle size of less than the average, by number/intensity, i.e., less than about 200 nm, etc., when measured by the above-noted technique.

Example 6

Process for Producing Solid Nanostructured Aprepitant Particles

During the experiments Aprepitant nanoparticles were prepared in a microfluidic based continuous flow reactor. As a starting solution, 1400 mg of Aprepitant, 700 mg of sodium dodecyl sulfate and 7000 mg of Soluplus® was dissolved in 100 ml of ethanol. The prepared solution was passed into the reactor unit with 3.0 mL/min flow rate using a feeding unit. Meanwhile, using a second feeding unit, distilled water was passed into a mixing unit with 40.0 mL/min flow rate, where it was mixed with the solution containing Aprepitant coming from the first reactor unit. The nanoparticles were continuously produced at atmospheric pressure at 50 C.° due to the chemical precipitation by water passed into the mixing unit. The produced colloidal solution driven through the second reactor unit getting to the dynamic light scattering unit (Nanotrac) integrated to the device, which can detect the particle size of the obtained nanoparticle continuously. The size of the nanoparticles can be controlled in wide range by changing the flow rates; pressure and the types of the stabilizers. The average particles size of the Aprepitant particles was 75 nm in the best case (FIG. 2).

The colloid solution was solid formulated using rotary evaporation and freeze drying. The solid powder was redispersed in distilled water and the particle size of the redispersed colloid solution was determined using dynamic light scattering (Nanotrac). The average particles size of the Aprepitant particles was 79 nm (FIG. 2).

The invention claimed is:

1. A stable nanostructured aprepitant composition comprising aprepitant, sodium dodecyl sulfate and polyvinyl caprolactam-polyvinyl acetate-polyethylene glycol graft copolymer, which composition is obtained by the following steps in a microfluidic based continuous flow reactor:
   a) aprepitant, sodium dodecyl sulfate and polyvinyl caprolactam-polyvinyl acetate-polyethylene glycol graft copolymer are dissolved in ethanol, thereby forming a solution;
   b) the solution in step a) is passed into a reactor unit using a first feeding unit;
   c) meanwhile, using a second feeding unit, distilled water is passed into a mixing unit, where the distilled water is mixed with effluent containing aprepitant coming from the reactor unit, wherein the ratio of the flow rate in the first feeding unit to the flow rate in the second feeding unit is 3.0:40.0;
   wherein the nanostructured aprepitant composition has an average particle size of less than about 200 nm,
   a solubility at least about 0.1 mg/ml in FassiF and at least 0.4 mg/mL in FessiF solution,
   in vitro permeability through artificial membrane at least $1*10^{-6}$ cm/s in FassiF condition and at least $1*10^{-6}$ cm/s in FessiF condition
   instantaneous redispersibility in a physiological medium,
   reduced or eliminated fed/fasted effect,
   at least bioequivalent absorption in human gastrointestinal tract and faster onset of action compared to the reference or marketed compound.

2. The stable nanostructured aprepitant composition according to claim 1 wherein the flow rate in the first feeding unit is 3.0 mL/min and the flow rate in the second feeding unit is 40.0 mL/min.

3. A stable nanostructured aprepitant composition according to claim 1 further comprising an additional stabilizer for steric and electrostatical stabilization.

4. A process for the preparation of the composition according to claim 1, comprising the following steps:
   a) aprepitant, sodium dodecyl sulfate and polyvinyl caprolactam-polyvinyl acetate-polyethylene glycol graft copolymer are dissolved in ethanol, thereby forming a solution;
   b) the solution in step a) is passed into a reactor unit using a first feeding unit;
   c) meanwhile, using a second feeding unit, distilled water is passed into a mixing unit, where the distilled water is mixed with effluent containing aprepitant coming from the reactor unit, wherein the ratio of the flow rate in the first feeding unit to the flow rate in the second feeding unit is between 3.0:40.0.

5. The process according to claim 4 wherein the flow rate in the first feeding unit is 3.0 mL/min and the flow rate in the second feeding unit is 40.0 mL/min.

6. A pharmaceutical composition comprising a nanostructured composition according to claim 1 together with pharmaceutically acceptable auxiliary materials, in the form of oral, pulmonary, rectal, parenteral, intracisternal, intravaginal, intraperitoneal, ocular, otic, local, buccal, nasal or topical administration.

7. A method for the treatment of a subject in need thereof by administering to the subject an effective amount of nanostructured aprepitant composition according to claim 1 or the pharmaceutical composition comprising a nanostructured composition according to claim 1.

8. The method according to any of claim 7 for prevention of acute and delayed chemotherapy-induced nausea and vomiting and for prevention of postoperative nausea and vomiting.

9. The method according to claim 7, wherein the composition has
   a solubility at least about 0.1 mg/ml in FassiF and at least 0.4 mg/mL in FessiF solution, in vitro permeability through artificial membrane at least $1*10^{-6}$ cm/s in FassiF condition and at least $1*10^{-6}$ cm/s in FessiF condition instantaneous redispersibility in a physiological medium, reduced or eliminated fed/fasted effect, at least bioequivalent absorption in human gastrointestinal tract compared to the reference or marketed compound, faster onset of action, for decreasing the dosage used.

* * * * *